United States Patent [19]

Letton et al.

[11] Patent Number: 5,102,683

[45] Date of Patent: Apr. 7, 1992

[54] FATTY COMPOSITIONS WITH HIGH SOLIDS CONTENT

[75] Inventors: James A. Letton; Joseph McGrady, both of Forest Park; David J. Weisgerber, Cincinnati, all of Ohio

[73] Assignee: The Procter & Gamble Company, Cincinnati, Ohio

[21] Appl. No.: 589,858

[22] Filed: Sep. 28, 1990

Related U.S. Application Data

[63] Continuation of Ser. No. 288,840, Dec. 22, 1988, abandoned.

[51] Int. Cl.⁵ .................... A23D 9/00; A23L 1/308
[52] U.S. Cl. .................... 426/601; 426/606; 426/607; 426/804
[58] Field of Search .......... 426/601, 606, 607, 804; 514/552; 260/410.6

[56] References Cited

U.S. PATENT DOCUMENTS 4,005,195  1/1977  Jandacek ..................... 426/658 X
4,734,287  3/1988  Singer et al. ................. 426/602 X

FOREIGN PATENT DOCUMENTS 233856  2/1987  European Pat. Off.

OTHER PUBLICATIONS

Lees, R. and Jackson, E. B., 1973, "Sugar Confectionery and Chocolate Manufacture", Leonard Hill, Glasgow, pp. 133–137.

Primary Examiner—Donald E. Czaja
Assistant Examiner—Evan Federman
Attorney, Agent, or Firm—Karen F. Clark; Ronald L. Hemingway; Richard C. Witte

[57] ABSTRACT

Edible compositions comprising solid and liquid fatty materials, and having a high solids content, said solids having a particle size of 10 microns or less. Preferably, the fatty materials are wholly or partially non-digestible.

17 Claims, No Drawings

FATTY COMPOSITIONS WITH HIGH SOLIDS CONTENT

This is a continuation of application Ser. No. 288,840, filed on Dec. 22, 1988 now abandoned.

FIELD OF THE INVENTION

This invention pertains to edible compositions comprising solid and liquid fatty materials and having a high solids content. Preferably, the fatty materials are wholly or partially non-digestible.

BACKGROUND OF THE INVENTION

There is an ever-increasing interest among consumers in food products having a reduced fat and reduced calorie content. Certain edible, but non-absorbable and non-digestible liquid materials have been found to be suitable as fat substitutes and as pharmaceutical compositions for the treatment of hypercholesterolemia. See, for example, U.S. Pat. No. 3,600,186 (issued Aug. 17, 1971), and U.S. Pat. No. 3,954,976 (issued May 4, 1976), both of Mattson and Volpenhein, both assigned to Procter & Gamble, and both incorporated herein by reference. In order to alleviate undesirable anal leakage effects associated with the ingestion of food products containing certain of these liquid fatty materials, an improved fat substitute was achieved by incorporating certain solid fatty materials into these liquid fatty materials. See, for example, U.S. Pat. No. 4,005,195 of Jandacek (issued Jan. 25, 1977), assigned to The Procter & Gamble Company, and incorporated by reference herein. The preferred ratio of liquids to solids in the Jandacek compositions is from about 4:1 to about 2:1. While said mixture of liquids and solids satisfactorily corrected the problem of anal leakage, the inclusion of such high levels of solid fatty materials in the liquid fatty materials resulted in a fat substitute which, although substantially devoid of undesirable anal leakage effects, sometimes tended to yield an undesirable waxy or gritty sensation in the mouth upon ingestion by the consumer.

It is therefore an object of this invention to create a wholly or partially non-digestible fatty composition suitable for incorporation into food compositions which substantially alleviates the undesired effect of anal leakage and substantially eliminates the waxy or gritty sensation in the mouth upon ingestion.

This and other objects of the invention will become clear by the disclosure herein.

All percentages and ratios are by weight unless otherwise indicated.

SUMMARY OF THE INVENTION

The present invention relates to an improved fatty composition. The composition comprises a liquid fatty material which is preferably non-digestible and a solid fatty material. The solid fatty material can be digestible or non-digestible The improved fatty composition exhibits substantially no waxiness or grittiness sensation in the mouth, yet the composition retains the anti-anal leakage benefit imparted by the inclusion of the solid fatty materials in non-digestible liquid fatty material. This is achieved by incorporating solid fatty materials having a particle size of 10 microns or less.

Said fatty composition therefore comprises a mixture of liquid fatty material which is preferably wholly or partially non-digestible and a solid fatty material wherein the solid material has a particle size of 10 microns or less and wherein the weight ratio of liquid fatty material to solid fatty material is from about 1.5:1 to about 4:1.

The benefits of this invention are achieved with a maximal reduction of calories, as compared to conventional triglyceride fats, when both the liquid fatty material and the solid fatty material are wholly or partially non-digestible. There is less of a caloric reduction when a solid fatty material which is digestible is suspended in a non-digestible liquid fatty material. Furthermore, as compared to conventional triglyceride fats, there is a substantially less reduction in calories when a non-digestible solid fatty material is suspended in a digestible liquid fatty material (rather than a wholly or partially non-digestible liquid fatty material) and there is no caloric reduction when a digestible solid fatty material is suspended in a digestible liquid fatty material.

The term "solid fatty material" as used herein means a material selected from solid triglyceride fats conventionally present in the human diet as well as solid edible non-digestible materials which can replace triglyceride fats in foods and still provide the gustatory and physical properties of triglyceride fat, such as lubricity and flavors, in the human diet. By "solid" herein, it is meant that the material has a complete melting point above 37° C. (98.6° F.). The solid fatty materials impart anal leakage control when added to the non-digestible liquid fatty materials. In a preferred aspect, the invention described herein is directed to a fatty composition wherein the liquid component is a non-digestible oil and which exhibits desirable anti-anal leakage effects because of the solid fatty materials present therein but does not exhibit the waxy or gritty sensation normally associated with the inclusion of solids.

The term "liquid fatty material" as used herein means a material selected from liquid triglyceride oils conventionally present in the human diet and certain edible oils which are non-digestible (either wholly or partially), and which can replace the regular liquid triglycerides in the human diet. The wholly or partially non-digestible oils are preferred. These preferred materials can replace conventional triglyceride oils in the diet and still provide the gustatory and physical properties of triglyceride oils, such as lubricity and flavors. By "liquid" herein is meant that the material has a melting point of 37° C. (98.6° F.) or below.

By "non-digestible" as used herein is meant that at least 70% of the material (and preferably all of the material) is not digested by the body. Said material passes through the digestive system substantially the same as when it was ingested. Conversely, by "digestible" is meant that more than 30% of the material is digested by the body.

By "anti-anal leakage (AAL) agents" as used herein is meant edible materials which prevent leakage of non-digestible liquid fatty materials through the anal sphincter. The solid fatty materials, either fully-, partially-, or non-digestible, herein perform as anti-anal leakage agents for the non-digestible liquid fatty materials.

The fatty composition of this invention comprises a stable solid/liquid dispersion which is a mixture of solid fatty materials, having a particle size of 10 microns or less, and liquid fatty materials, wherein the weight ratio of said liquids to said solids is from about 1.5:1 to about 4:1 and wherein the liquids are preferably non-digestible. This stable solid/liquid system provides effective control against anal leakage of the liquid non-digestible fatty materials and at the same time alleviates the detection of grittiness or waxiness in the mouth.

DETAILED DESCRIPTION OF THE INVENTION

The present invention is directed to a fatty composition comprising a mixture of a liquid fatty material which is preferably non-digestible and which has a melting point of 37° C. (98.6° F.) or below and a solid fatty material which has a complete melting point higher than 37° C. (98.6° F.). The weight ratio of the liquid fatty material to the solid fatty material is from about 1.5:1 to about 4:1. The solid fatty material has a particle size of less than about 10 microns. This small particle size enhances the anti-anal leakage benefit imparted by the solid fatty materials when suspended in non-digestible liquid fatty material. Also, for both solid digestible and solid non-digestible materials, the small particle size avoids the gritty sensation in the mouth often associated with the solid materials.

To achieve the specified particle size of 10 microns or less, the solid fatty materials are preferably milled, more preferably ball milled, most preferably in the presence of glass or ceramic beads, either before or after they are added to the liquid fatty materials. Although various types of size reduction equipment can be used, the mills should ideally utilize either glass or ceramic beads in order to attain the specified particle size of 10 microns or less. During the milling operation, it is imperative that the temperature be maintained at least about −12.2° C. (10° F.), preferably about −9.4° C. (15° F.), below the complete melt point of the solid fatty materials in order to gain the benefits of the invention described herein. For this reason, although the solid fatty materials can be satisfactorily milled alone before being added to the liquid fatty materials, it is preferable to combine the solid and liquid fatty materials in slurry form and subject the slurry to milling. This method of preparation yields a mixture more easily retrievable from the mill than is the case with milled solid fatty materials alone, and facilitates the control of temperature due to the effect of the liquid fatty materials upon heat transfer.

It is important to realize that the benefits of this invention are determined by the solid fatty material having a particle size of 10 microns or less. It is immaterial, however, how this particle size is achieved. While milling is one method of achieving a particle size of 10 microns or less, any method of attaining a solid fatty material having the requisite particle size is suitable for use in preparing the solid fatty material contained in the fatty composition of the present invention.

As has been previously stated, liquid fatty materials which are digestible can be used satisfactorily in the present invention, although the use of liquid fatty materials which are non-digestible is certainly most preferred. The use of the non-digestible fatty materials described herein results in an improved fatty composition which exhibits less fat and calories as compared to conventional triglyceride fats, and is therefore preferred. However, the use of non-digestible liquid fatty materials in the absence of solid fatty materials often results in anal leakage of these non-digested liquid fatty materials; this problem is solved by the incorporation of solid fatty materials into the non-digestible liquid fatty materials. Both digestible and non-digestible solid fatty materials, or a mixture thereof, successfully alleviate the anal leakage problem, but the use of non-digestible solid fatty materials results in greater fat and calorie reduction than does the use of digestible solid fatty materials.

The present invention is directed to an improved fatty composition comprising solid and liquid fatty materials wherein the waxy or grainy sensation in the mouth typically associated with the inclusion of solid fatty materials is alleviated by use of solid fatty materials having a particle size of 10 microns or less. The liquid fatty materials are preferably non-digestible in order to achieve fat and calorie reduction, although the use of digestible liquid fatty materials can be employed. The liquid fatty materials can also consist of a blend of non-digestible liquid fatty materials and digestible liquid fatty materials. When digestible liquid fatty materials alone are utilized, fat and calorie reduction are sacrificed, but there is no anal leakage problem. In this instance, the use of solid fatty materials to alleviate anal leakage is obviously unnecessary, but the presence of solid fatty materials provides desirable textures or flavors to the digestible liquid fatty materials.

In order to realize maximum benefits of the present invention, the use of non-digestible liquid fatty materials in the improved fatty composition of the present invention is most preferred. Either non-digestible or digestible solid materials having a particle size of 10 microns or less may be added thereto, but the use of non-digestible solid fatty materials results in a maximum reduction of fat and calories.

NONDIGESTIBLE FATTY MATERIALS

A wide variety of non-digestible fatty materials are suitable for use in the fatty compositions of the present invention. Depending on their melting point, they can be used as a liquid fatty material or as a solid fatty material, or both, in the compositions of the invention. Examples of such non-digestible fatty materials are: fatty alcohol esters of polycarboxylic acids (U.S. Pat. No. 4,508,746 of Hamm, issued Apr. 2, 1985); fatty polyesters of polyglycerol (U.S. Pat. No. 3,932,532 of Hunter et al., issued Jan. 13, 1976) (food use disclosed in German Patent 207,070, issued Feb. 15, 1984); ethers and ether-esters of polyols containing the neopentyl moiety (U.S. Pat. No. 2,962,419 of Minich, issued Nov. 29, 1960); fatty alcohol diesters of dicarboxylic acids such as malonic and succinic acid (U.S. Pat. No. 4,582,927 of Fulcher, issued Apr. 15, 1986); triglyceride esters of alpha branched chain-alkyl carboxylic acids (U.S. Pat. No. 3,579,548 of Whyte, issued May 18, 1971), and sugar and sugar alcohol fatty acid polyesters (U.S. Pat. No. 3,600,186 of Mattson and Volpenhein, issued Aug. 17, 1971), all incorporated herein by reference. The fatty moieties of these materials typically contain from about 8 to about 24 carbon atoms, preferably from about 14 to about 18 carbon atoms.

For reasons of cost efficiency, consumer acceptability, and assurance of inherent safety, the preferred class of such materials to be used in the fatty composition of the present invention is polyol fatty acid polyesters. Polyol fatty acid polyesters comprise sugar fatty acid polyesters, sugar alcohol fatty acid polyesters, polyglycerol fatty acid polyesters, and mixtures thereof.

Sugar, sugar alcohol, or polyglycerol fatty acid polyesters are among the preferred materials for use in the present invention. The term "sugar" is used herein in its conventional sense as generic to mono- and disaccharides. The term "sugar alcohol" is likewise used in its conventional sense as generic to the reduction product of sugars wherein the aldehyde or ketone group has been reduced to an alcohol. The term "polyglycerol" is used to describe mixtures of ethers of glycerol with itself, ranging from 2 to 30 glycerol units per molecule Polyglycerol is prepared by polymerization of glycerol in the presence of either acid or base with the removal of water during reaction. For example, the synthesis described in U.S. Pat. No. 3,968,169 of Seiden and Martin (assigned is suitable and is incorporated by reference herein. Polyglycerol can be fractionated by methods known in the art, such as molecular distillation, to give specific polymer ranges.

The polyol polyester compounds suitable for use as the fatty materials herein are prepared by reacting a monosaccharide, disaccharide, sugar alcohol, or polyglycerol with such fatty acids as will be disclosed herein. Preferred monosaccharides, disaccharides, and sugar alcohols contain 4 to 8 hydroxyl groups. Preferred polyglycerols contain predominantly about 5 to about 15, and more preferably about 6 to about 10, etherified glycerol units.

Examples of suitable monosaccharides are those containing 4 hydroxyl groups such as xylose, arabinose and ribose; the sugar alcohol derived from xylose, i.e., xylitol, is likewise suitable. The monosaccharide erythrose is not suitable for use in the fatty materials of the fatty composition of the present invention since it only contains 3 hydroxyl groups; however, the sugar alcohol derived from erythrose, i.e., erythritol, contains 4 hydroxyl groups and is thus suitable. Among the 5 hydroxyl-containing monosaccharides that are suitable for use herein are glucose, mannose, galactose, fructose, and sorbose. A sugar alcohol derived from sucrose, glucose, or sorbose, e.g., sorbitol, contains 6 hydroxyl groups and is also suitable as the alcohol moiety of the fatty acid ester compound Examples of suitable disaccharides are maltose, lactose, and sucrose, all of which contain 8 hydroxyl groups.

In preparing the sugar, sugar alcohol, or polyglycerol fatty acid polyesters for use in the present invention, a sugar, sugar alcohol, or polyglycerol, such as those identified immediately above, must be esterified with fatty acids, i.e., aliphatic terminal monocarboxylic acids, having from about 2 to about 24, preferably from about 8 to about 24, most preferably from 14 to 18, carbon atoms. The fatty acids can be derived from suitable or naturally occurring or synthetic fatty acids and can be saturated or unsaturated, including positional and geometric isomers. Examples of such fatty acids are caprylic, capric, lauric, myristic, myristoleic, palmitic, palmitoleic, stearic, oleic, elaidic, ricinoleic, linoleic, linolenic, eleostearic, arachidic, behenic, erucic and brassidic. The sugar, sugar alcohol, or polyglycerol esters will be liquids or solids depending upon the particular combination of polyol and esterifying acids, as well as the degree of esterification.

Fatty acids per se or naturally occurring fats and oils can serve as the source for the fatty acid component in the sugar, sugar alcohol, or polyglycerol fatty acid ester. For example, rapeseed oil provides a good source of $C_{22}$ fatty acid, while $C_{16}$–$C_{18}$ fatty acids can be provided by tallow, soybean oil, palm oil, or cottonseed oil. Shorter chain fatty acids can be provided by coconut, palm kernel, or babassu oils. Corn oil, lard, canola, olive oil, peanut oil, safflower seed oil, sesame seed oil, and sunflower seed oil are examples of other natural oils which can serve as the source of the fatty acid component.

Sugar, sugar alcohol, or polyglycerol fatty acid polyesters suitable for use as the fatty material in the fatty composition of the present invention described herein can be prepared by a variety of methods known to those skilled in the art. These methods include, for example, transesterification of the polyol with methyl, ethyl, or glycerol fatty acid esters using a variety of catalysts; acylation of the polyol with a fatty acid anhydride; and acylation of the polyol with a fatty acid, per se. Polyol polyesters, their use as fat substitutes, and their preparation are described in detail in the following U.S. Patents, all assigned to The Procter & Gamble Company, and all incorporated by reference herein: U.S. Pat. No. 3,600,186 to Mattson and Volpenhein, issued Apr. 23, 1968; U.S. Pat. No. 4,034,083 to Mattson, issued July 5, 1977; U.S. Pat. No. 2,831,854 to Tucker and Martin, issued Apr. 22, 1958; U.S. Pat. No. 3,963,699 to Rizzi and Taylor, issued June 15, 1976; and U.S. Pat. Nos. 4,518,772 issued May 21, 1985, and 4,517,360 issued May 14, 1985, both to Volpenhein; and U.S. Pat. No. 3,968,169 to Seiden and Martin, issued July 6, 1976.

A characterizing feature of the sugar or sugar alcohol fatty acid polyesters useful in the fatty composition of this invention is that they predominantly contain at least 4 fatty acid ester groups. Sugar or sugar alcohol fatty acid polyester compounds that contain 3 or less fatty acid ester groups are digested in the intestinal tract much in the same manner as ordinary triglyceride fats, but sugar or sugar alcohol fatty acid polyester compounds that contain four or more fatty acid ester groups are digested to a lesser extent, or not at all. It is not necessary that all of the hydroxyl groups of the sugar or sugar alcohol fatty acid polyester be esterified with fatty acids, but it is preferable that the sugar or sugar alcohol fatty acid polyester contain no more than three unesterified hydroxyl groups, more preferable that it contain no more than two, and most preferable that substantially all of the hydroxyl groups of the sugar or sugar alcohol fatty acid polyester is esterified with fatty acid. Therefore, sugar or sugar alcohol fatty acid polyesters are preferred materials for use in the present invention as both the liquid and solid fatty materials because, by being substantially non-digestible, they are absorbed to a very low extent, or not at all, and result in a reduced- or non-caloric fatty composition.

A characterizing feature of the polyglycerol fatty acid polyesters useful in this invention is that they predominantly contain at least 5, preferably from about 5 to about 15, and most preferably from about 6 to about 10, etherified glycerol units In addition, polyglycerol fatty acid polyesters useful in this invention should have at least 75%, and preferably at least 85%, of their hydroxyl groups esterified with fatty acids. Polyglycerol fatty acid polyester compounds that contain 3 or less etherified glycerol units are digested, absorbed, and metabolized much in the same manner as ordinary triglyceride fats, but polyglycerol fatty acid polyester compounds that contain 5 or more etherified glycerol units are digested, absorbed, and metabolized to a much lesser extent, or not at all. Therefore, polyglycerol fatty acid polyesters are also preferred materials for use in the present invention as both the liquid and solid fatty materials because, by being substantially non-digestible, they are absorbed to a lesser extent, or not at all, and result in a reduced- or non-caloric fatty composition.

The above described fatty materials may exist in solid or liquid forms at body temperature, i.e., at 37° C. (98.6° F.), depending upon their particular polyol and fatty acid compositions. Discussed herein below are certain preferred solid and liquid fatty materials for use in the improved fatty composition of the present invention.

SOLID FATTY MATERIALS

The solid fatty materials for use in the present invention are solid at body temperature, i.e., have a complete melting point higher than 37° C. (98.6° F.). These solid fatty materials are selected from solid triglyceride fats conventionally present in the human diet as well as solid edible non-digestible materials which can replace triglyceride fats in foods and still provide the gustatory and physical properties of triglyceride fat, such as lubricity and flavors, in the human diet.

The solid digestible sources of the solid fatty acids produce solid free fatty acids in the gut during digestion, and these function as anti-anal leakage agents. The solid non-digestible fatty materials remain in their solid non-digested form as they pass through the digestive tract and thereby also function as anti-anal leakage agents.

Solid fatty materials having a particle size of 10 microns or less are combined with the liquid fatty materials. A stable solid/liquid dispersion is produced in which separation of the solid and liquid components is prevented. Prevention of separation is important from the standpoint of achieving improved anal leakage control when non-digestible liquid fatty materials are employed It is also important from the standpoint of product acceptance by consumers. For example, a shortening or margarine which separates into liquid and solid phases during storage would have poor consumer acceptance. The composition of the present invention achieves both good liquid/solid stability and avoidance of grittiness or waxiness in the mouth.

Non-limiting examples of solid fatty acids and digestible sources thereof which can be used as the solid fatty material herein include the free fatty acids per se, compounds such as esters (e.g., triglycerides) that yield such fatty acids on hydrolysis in the gut, soaps of the fatty acids such as the sodium, potassium, etc., water-soluble soaps, as well as the calcium and magnesium water-insoluble soaps. Highly preferred herein for their anti-anal leakage effect are the $C_{16}$–$C_{26}$, most preferably the $C_{16}$–$C_{18}$, saturated or trans-unsaturated fatty acids, or edible sources thereof.

While the composition of the fatty acids of the solid fatty materials render them effective as anti-anal leakage (AAL) agents, reduction of the particle size of said solid fatty material increases the surface area of said solid fatty material This increase in surface area entraps the liquid fatty materials, forming a stable liquid/solid dispersion. This stable liquid/solid dispersion diminishes the detection of waxiness or grittiness in the mouth and enhances the effectiveness of the solid fatty material as an AAL agent.

Specific examples of materials suitable for use as solid fatty material in the fatty composition of the invention herein include solid natural or processed digestible fats yielding $C_{12}$–$C_{24}$ saturated fatty acids in the gut, e.g., materials such as hydrogenated tallow, tallow, lard, enriched concentrates of triglycerides having high levels of saturated fatty acids obtainable from these sources, and sources such as highly saturated cottonseed oil or palm oil fractions obtained by processes such as crystallization or directed rearrangement which yield the desired higher concentrations of the more saturated fatty acids in the resulting "hardstock" fractions. Such materials are all available by well-known processes.

Partially hydrogenated or elaidinized olive oil, soybean oil, sunflower seed oil, safflower seed oil, rapeseed oil, palm oil, or palm kernel oil, or such materials which are hydrogenated or elaidinized and concentrated, for example by crystallization, to provide fractions which are enriched in sources of the longer-chain, substantially saturated or trans-unsaturated fatty acids, are all useful as the solid fatty material in the invention described herein. (By "substantially hydrogenated" herein is meant oils having an Iodine Value of Ca. 50, or lower.)

Of course, any of the foregoing unsaturated oils are useful herein after they have been substantially completely hydrogenated to convert the unsaturated fatty acid ester groups to the corresponding saturated fatty acids or have been substantially completely elaidinized to convert the unsaturated fatty acid ester groups from the geometric cis- to the corresponding trans-form.

Synthetic solid digestible or non-digestible fatty materials, especially fatty acid esters made from the $C_{12}$–$C_{24}$, more preferably $C_{16}$–$C_{22}$, most preferably $C_{16}$–$C_{18}$, saturated or trans-unsaturated fatty acids are likewise useful as the solid fatty materials for use in the invention described herein. Such materials include the solid digestible or non-digestible esters of tetrahydric alcohols such as erythritol, esters of pentahydric alcohols such as xylitol, and erythritol, and esters of hexahydric alcohols such as sorbitol, and the like.

Typical examples of edible, non-digestible, solid fatty materials useful as the solid fatty material herein include sucrose octastearate, sucrose octapalmitate, sucrose heptastearate, xylitol pentastearate, galactose pentapalmitate, sucrose octaelaidate, the sucrose octaesters of mixed saturated $C_2$ to $C_{24}$, preferably $C_8$ to $C_{24}$, fatty acids and the like.

Another highly preferred solid fatty material comprises edible, non-digestible, solid sucrose fatty acid polyesters in which the fatty groups consist essentially of short chain fatty acid radicals containing from about 2 to about 10 carbon atoms and long chain fatty acid radicals containing from about 20 to 24 carbon atoms, the molar ratio of short chain to long chain radicals being from about 4:4 to about 3:5 and the degree of esterification being from about 7 to about 8. These compounds can be made by a variety of methods known to those skilled in the art such as those methods cited hereinabove. When using the methyl ester route for preparing these compounds, the octaester of the short chain fatty acid is prepared first, then this product is partially interesterified with the methyl ester of the long chain fatty acid in order to obtain the sucrose ester of the mixed short chain/long chain fatty acids. These compounds are solid at temperatures above about 40° C. (104° F.). They have the ability to trap large amounts of liquid oil within their crystal structure.

Another type of solid fatty material suitable for use in the fatty composition described herein comprises fatty acid esters which are non-digestible by virtue of branching on the alpha-carbon atom of the fatty acid moiety Such materials, which are well known in the chemical arts, include, for example, solid alpha-methyl and alpha, alpha-dimethyl $C_{10}$–$C_{18}$ fatty acid esters of lower alcohols such as ethanol and of polyols such as glycerol.

The polyol fatty acid polyesters suitable for use as the solid fatty material in the fatty composition of the present invention are preferably esterified with particular kinds of fatty acids Preferably, at least about 80%, and, most preferably, at least 90%, of the fatty acids are selected from the group consisting of mixtures of $C_{16:0}$, $C_{18:0}$, $C_{18:1}$, $C_{18:2}$, $C_{22:0}$, $C_{22:1}$, their geometric and positional isomers, and mixtures thereof.

Highly preferred solid fatty materials for use in the improved fatty composition of the present invention are sucrose fatty acid polyesters of $C_8$ to $C_{24}$ saturated fatty acids. Preferred sucrose fatty acid polyesters have the majority (i.e., more than 4) of their hydroxyl groups esterified with fatty acids. Preferably, in mixtures of the esters, at least about 85%, and most preferably about 95%, of the sucrose polyesters are selected from the group consisting of octaesters, heptaesters, and hexaesters, and mixtures thereof. Preferably, no more than about 35% of the esters are hexaesters or heptaesters, and at least about 60% of the polyesters are octaesters. Most preferably, at least about 70% of the polyesters are octaesters. It is also most preferred that the polyesters have a total content of penta- and lower esters of not more than 3%.

Solid polyglycerol fatty acid polyesters are another preferred class of compounds which may also be utilized as the solid fatty materials of the fatty composition of the present invention. Polyglycerol is prepared by the polymerization of glycerine in the presence of either acid or base. The polyglycerols can contain from 2 to 30 glycerol moieties. Preferably, the polyglycerols will be those having at least 5, more preferably from 5 to 15, and most preferably from about 6 to about 10, glycerol moieties.

The polyglycerol compounds can be made by any synthetic method. For example, that described in U.S. Pat. No. 3,968,169 of Seiden and Martin (assigned to Procter & Gamble), issued July 6, 1976 is suitable and is incorporated by reference herein. Esterification of the polyglycerols can also be performed by any method known to the art, providing the resulting polyglycerol esters have the properties required of the present invention.

LIQUID FATTY MATERIALS

The liquid fatty materials of the present invention are liquids at body temperature, i.e., have a melting point of about 37° C. (98.6° F.) or below. These liquid fatty materials are preferably any of a variety of edible, non-digestible compounds which can replace triglyceride fats or oils in the human diet. These materials provide the benefits of triglyceride fats and oils, i.e., lubricity and flavors, yet provide fewer or no calories because they are absorbed to a lesser extent or not at all.

Even though non-digestible liquid fatty materials are preferred for use herein, digestible liquid fatty materials may also be employed. While these materials do not exhibit anal leakage, they do not exhibit the fat and caloric reduction achieved when non-digestible liquid fatty materials are utilized. Examples of suitable digestible liquid fatty materials are vegetable oils such as soybean oil, cottonseed oil, and rapeseed oil.

Preferably, the non-digestible liquid fatty material is selected from the group consisting of polyol fatty acid polyesters and polycarboxylic acids esterified with fatty alcohols, and mixtures thereof. Preferred liquid polyol fatty acid polyesters are sugar fatty acid polyesters, sugar alcohol fatty acid polyesters, and polyglycerol fatty acid polyesters, and mixtures thereof. More preferably, the liquid fatty material is selected from the group consisting of sugar fatty acid polyesters and sugar alcohol fatty acid polyesters, and mixtures thereof. The sugars and sugar alcohols contain from 4 to 8 hydroxyl groups and at least 4 of the hydroxyl groups are esterified.

Preferred polyols for preparing liquid fatty materials for use in the present invention are selected from the group consisting of erythritol, xylitol, sorbitol, glucose and sucrose. Sucrose is especially preferred.

The polyol starting material having at least four hydroxyl groups must be esterified on at least four of the hydroxyl groups with a fatty acid containing from about 2 to about 24 carbon atoms, preferably from about 8 to about 24 carbon atoms, and most preferably from about 14 to about 18 carbon atoms. These fatty acids can be derived from naturally occurring fats or they can be synthetic fatty acids, including positional or geometrical isomers. Typically they are unsaturated or mixtures of unsaturated and saturated fatty acids. Examples of the fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid or mixtures thereof. In order to provide the liquid sucrose polyesters most highly preferred as the liquid fatty materials for use in the fatty composition of the present invention, at least about half of the fatty acids incorporated into a polyester molecule must be unsaturated. Oleic and linoleic acids, and mixtures thereof, are especially preferred unsaturated fatty acids.

The liquid polyol fatty acid polyesters useful as the liquid fatty material of this invention must contain at least four fatty acid ester groups. Polyol fatty acid polyester compounds that contain three or less fatty acid ester groups are digested and the products of digestion are absorbed from the intestinal tract much in the manner as ordinary trillyceride fats, whereas the polyol fatty acid polyester compounds that contain four or more fatty acid ester groups are substantially non-digestible and consequently non-absorbable by the human body. It is not necessary that all of the hydroxyl groups of the polyol be esterified with fatty acid, but it is preferable that the polyol contain no more than three unesterified hydroxyl groups, and more preferable that it contain no more than two unesterified hydroxyl groups. Most preferably, substantially all of the hydroxyl groups of the polyol are esterified with fatty acid, i.e., the compound is substantially completely esterified. The fatty acids esterified to the polyol molecule can be the same or mixed (but, as noted above, a substantial amount of the unsaturated acid ester groups must be present to provide liquidity).

The following are non-limiting examples of specific liquid polyol fatty acid polyesters containing at least four fatty acid ester groups suitable for use as the liquid fatty material in the fatty composition of the present invention: sucrose tetraoleate, sucrose pentaoleate, sucrose hexaoleate, sucrose heptaoleate, sucrose octaoleate, sucrose octaelaidate, glucose tetraoleate, the glucose the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

As noted above, highly preferred liquid polyol fatty acid esters are those wherein the fatty acids contain from about 14 to about 18 carbon atoms.

The polyol fatty acid polyesters suitable for use herein as liquid fatty materials can be prepared by a variety of methods known to those skilled in the art. These methods include transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. As an example, the preparation of polyol fatty acid esters is described in U.S. Pat. Nos. 2,831,854, 3,963,699, 4,517,360 and 4,518,772 (all herein incorporated by reference).

Specific, but non-limiting, examples of the preparation of liquid polyol fatty acid esters suitable for use in the practice of this invention are as follows.

Erythritol tetraoleate—Erythritol and a five-fold molar excess of methyl oleate are heated at 180° C. under vacuum, with agitation, in the presence of sodium methoxide catalyst over two reaction periods of several hours each. The reaction product (predominately erythritol tetraoleate) is refined in petroleum ether and crystallized three times from several volumes of acetone at 1° C.

Xylitol pentaoleate—Xylitol and a five-fold molar excess of methyl oleate in dimethylacetamide (DMAC) solution are heated at 180° C. for five hours in the presence of sodium methoxide catalyst, under vacuum. During this time the DMAC is removed by distillation. The product (predominately xylitol pentaoleate) is refined in petroleum ether solution and, after being freed of petroleum ether, is separated as a liquid layer four times from acetone at ca. 1° C. and twice from alcohol at ca. 10° C.

Sorbitol hexaoleate is prepared by essentially the same procedure used to prepare xylitol pentaoleate except that sorbitol is substituted for xylitol.

Sucrose octaoleate is prepared by substantially the same procedure as that used to prepare erythritol tetraoleate except that sucrose is substituted for erythritol.

Polyglycerol fatty acid esters can also be used as the liquid fatty material for use in the fatty composition of the present invention. Polyglycerol is prepared by the polymerization of glycerine in the presence of either acid or base. The polyglycerols preferably contain from about 5 to about 15, most preferably about 6 to about 10, glycerol moieties.

The polyglycerol compounds can be made by any synthetic method. See, for example, U.S. Pat. No. 3,968,169 to Seiden and Martin (1976). Esterification of the polyglycerols can also be done by any method known to the art, providing the resulting polyglycerol esters have the properties required of the present invention.

Also useful as the present liquid fatty material are polycarboxylic acids esterified with fatty alcohols, where the acids are tricarboxylic and tetracarboxylic acids and higher. The polycarboxylic acids can be partially or wholly esterified with fatty alcohols. At least three fatty alcohol ester groups must be on an acid molecule to make it partially non-digestible.

The fatty compositions herein can be prepared by simple mixing of liquid fatty material with the solid fatty material having a particle size of 10 microns or less. Alternatively, the liquid fatty material can be mixed with the solid fatty material having a particle size of greater than 10 microns and then the mixture can be subjected to milling to reduce the particle size of the solid fatty material to 10 microns or less. In other words, the particle size of the solid fatty material can be reduced to 10 microns or less before or after mixing with the liquid fatty material.

The fatty compositions of the present invention can be used as a complete or partial replacement for the fat portion of foods which contain fat and non-fat ingredients for calorie reductions in such compositions. Examples of foods in which the fatty compositions herein can be used as a partial or total fat replacement are peanut butter, mayonnaise, snack dips, salad dressings, sauces, margarines, puddings, yogurts, ice creams, and related dairy products, and non-dairy whipped toppings.

The invention will be illustrated by the following examples:

EXAMPLE I

Synthesis of Solid Non-Digestible Fatty Material

Equipment

1 - 12 Liter, 3 neck glass reactor (Ace Glass, Inc., Louisville, KY, Model 6944)
1 - 5 Liter, 3 neck glass reactor (Ace Glass, Inc., Louisville, KY, Model 6944) equipped with mechanical agitator and heating mantel (Glas-Col, Inc., Model M-114)
1 - DuoSeal ® Vacuum Pump (Sargent Welch Scientific Co., Skokie, IL, Model 1402)
1 - 29/42 cold water condenser for refluxing methanol
1 - 3 Liter, 3 neck glass reactor (Ace Glass, Inc., Louisville, KY, Model 6944)
2 - 40/50 large vacuum cold traps with ¾ inch vapor take off/entry
1 - Tube Silicone-based high vacuum grease
1 - McLeod gauge (0–5 mm Hg) manometer
1 - Jar "Stir-Lube" ® Trubor lubricant (Ace Glass, Inc., Louisville, KY)
- Various high vacuum tubing for vacuum system
- Assorted beakers for material addition
- Lab jacks for heat mantel support and various clamps Reaction Materials 1. 6656.00 grams of starting stock soybean oil which has been hydrogenated to an Iodine Value (hereinafter I.V.) of 8
2. 175.00 grams of Baker's Special ® sugar (manufactured by Colonial Sugar Co., Gramercy, LA)
3. 200.00 milliliters of dry methanol
4. 25.00 grams of potassium hydroxide
5. 7.30 grams of potassium carbonate
6. 1664.00 grams of methanol
7. 33.28 grams of sodium methoxide
8. Approx. 30.00 grams Montmorillonite clay mix

A. Synthesis of Methyl Esters of Starting Stock Soybean Oil 6656.00 grams of hot (40°–60° C., 104°–140° F.) starting stock soybean oil was placed into a 12 liter reactor. The agitator was placed on the middle open neck, and agitation was begun. The Therm-O-Watch was placed on the first open neck and was set at 60° C. (140° F.). 1664.00 grams of methanol and 33.28 grams of sodium methoxide were mixed into a 4 liter glass beaker. After mixing was complete, the entire mixture was put into the reactor with the oil. The cold water condenser was next installed on the third open neck of the reactor and the Therm-0-Watch was set at 75° C. (167° F.). The mixture in the reactor was reacted for 1 hour at approx. 72° C. (161.6° F.). The reactants were allowed to cool to approx. 60° C. (140° F.) and then agitation was stopped. The glycerine mixture was allowed to settle on the bottom for approx. 30 minutes. The bottom layer was then siphoned off and discarded.

The reactor contents were washed twice, each time with 1500 milliliters hot water. At the end of each wash, the bottom layer in the reactor was siphoned off and discarded.

The crude product remaining in the reactor consisted of methyl esters and unreacted fatty acids. The crude product was dried under full vacuum at approx. 90° C. (194° F.) for 1 hour with vigorous agitation. The methyl esters were separated from the unreacted fatty acids by distilling the methyl esters under vacuum at approx. 170°-195° C. (338°-383° F.). The still bottoms remaining in the reactor contained the unreacted fatty acids and were discarded. The methyl esters are retained and subjected to the processes described in part B. below.

B. Synthesis of the Solid Non-Digestible Fatty Material from the Soybean Oil Methyl Esters 1929.00 grams of hot (60°-70° C., 140°-158° F.) methyl esters from part A. above were placed into a 5 liter reactor.

Agitation was started and the reactor was heated to 60° C. (140° F.). 25.00 grams of potassium hydroxide was dissolved in 200 milliliters of methanol and then added to the reactor. A cold water condenser was to react for 1 hour at approx. 73° C. (163.4° F.). 175.00 grams of Baker's Special ® Sugar and 7.30 grams of potassium carbonate was added to the reactor. The methanol was distilled out of the reactor by adding the 3 liter receiving reactor to the configuration with the cold water condenser in-line. When the methanol had stopped distilling, the vacuum system was set up with 40/50 traps in a dry ice/acetone bath. The heat-up of the reactor to 135° C.±1° C. (275°±33.8° F.) was then started.

When the reactor temperature had reached 85° C. (185° F.), the vacuum pump was started. The bleed line was left open. The system was monitored for foaming in the reactor. Foaming in the reactor was controlled by opening or closing the bleed as necessary. The process was allowed to run for a total of approx. 15 hours. Methanol, the by-product of the reaction, was collected in two dry ice traps.

At the end of the reaction period the reactants were cooled to approx. 80° C. (176° F.) and washed as follows: First, 800 milliliters water, 400 milliliters methanol, and 10.00 grams sodium chloride were added to the reactor mix and agitation was conducted for thirty minutes Agitation was ceased and the mixture was allowed to be separated. The top layer was the non-digestible fatty material and methyl esters and the bottom layer was methanol, water, unreacted sucrose, salt, and some lower esters of sucrose. The bottom layer was siphoned off and discarded. Second, 800 milliliters water, 400 milliliters methanol, and 10.00 grams sodium chloride was again added to the reactor mix and agitation was again conducted for thirty minutes After the agitation was stopped, the mixture was again allowed to separate. The top layer was the non-digestible fatty material and methyl esters and the bottom layer was methanol, water, unreacted sucrose, salt, and some lower esters of sucrose. The bottom layer was again siphoned off and discarded. Next, 400 milliliters hot (60° C., 140° F.) water and 15 grams of acetic acid were added to the reactor and mixed at 60° C. (140° F.) for 20 minutes.

The mixture was then allowed to separate. The bottom layer was siphoned off and discarded 400 milliliters of hot (approx. 60° C., 140° F.) water was added to the reactor and mixed for 20 minutes at approx. 60°-70° C. (140°-158° F.) The bottom layer was siphoned off and discarded.

The vacuum system was set up again, with dry ice traps, and the reactor heat-up to 90° C. (194° F.) to dry the mix was begun. The system was held at 90° C. (194° F.) for approx. 45 minutes 30 grams of Montmorillonite clay mix was added to the reactor and the contents of the reactor were then mixed at 90° C. (194° F.) for 15 minutes. This mixture was filtered by vacuum to purify the non-digestible fatty material/methyl ester mix.

Utilizing the 5 liter and 3 liter reactors, the vacuum system, and ice traps, a glass methyl ester stripper/deodorizer was set up utilizing the equipment in a reconfiguration. The mixture of the non-digestible fatty material and the methyl ester mix was placed into a clean 5 Liter reactor and was heated to approx. 180° C. (356° F.) while a nitrogen sparge and the vacuum system was operated. The bulk of the methyl esters were distilled from the non-digestible fatty material in approx. 2.5 hours.

The remaining mixture was next subjected to a steam sparge for approx. 4-5 hours, which reduced the level of methyl esters to approx. 500-1000 ppm.

The contents of the reactor was cooled and discharged into jars yielding the solid non-digestible fatty material.

The solid non-digestible fatty material synthesized as described herein had a melting point of about 60°-65° C. (140°-150° F.)

EXAMPLE II

Synthesis of Liquid Non-Digestible Fatty Material

A liquid non-digestible fatty material was made utilizing the same equipment, reaction materials, and processes of Example 1, except that the starting stock of soybean oil used (See Component #1 of the Reaction Materials in Example I) was hydrogenated to an I.V. of 107, as opposed to an I.V. of 8 as used in Example I to synthesize the solid non-digestible fatty materials.

The liquid non-digestible fatty material synthesized as described herein was liquid at room temperature, 25° C. (77° F.).

EXAMPLE III

Preparation of the Improved Fatty Composition Consisting of Solid and Liquid Non-Digestible Fatty Material The solid non-digestible fatty material as synthesized in Example I was broken into easy-to-handle chunks approx. 2-5 inches in diameter. 750 grams of these chunks were placed into a Vibro Energy Mill (manufactured by Sweco, Inc., Los Angeles, CA, Model DM 1) at room temperature, approx. 25° C. (77° F.). The mill was started and allowed to operate for approx. 7½ minutes, sufficient time to reduce the chunks to a size of 1 inch in diameter.

2250 grams of the liquid non-digestible fatty material synthesized in Example II was added into the mill at room temperature. The mill was started and allowed to operate for approx. 30-40 minutes, until the average particle size of the resulting slurry was less than or equal to 10 microns as measured under a light microscope.

The mill temperature was not allowed to exceed 48° C. (120° F.) at any time during this process.

EXAMPLE IV

Margarine Formulation Containing the Improved Fatty Composition

| COMPONENTS | Weight Percent |
|---|---|
| Improved Fatty Substance (Example III) | 60.100 |
| Oil Phase | |
| Span ® 60 (manufactured by ICI Americas, Inc., Wilmington, DE) | 1.740 |
| Tween ® 60 (manufactured by ICI Americas, Inc., Wilmington, DE) | 0.260 |
| Refined, bleached & deodorized soybean oil (I.V. 127-135) (manufactured by The Procter & Gamble Company, Cincinnati, Ohio) | 17.600 |
| Butter Flavors | 0.020 |
| Water Phase | |
| Potassium Sorbate | 0.100 |
| Citric Acid | 0.025 |
| Frodex ® (manufactured by American Maize Corp., Hammond, IN) | 0.100 |
| Non-Fat Dry Milk Solids | 1.000 |
| Sodium Chloride | 1.555 |
| Water | 17.500 |

The oil phase components are weighed into a stainless steel bowl and mixed while being heated to approx. 65° C. (150° F.). While the oil phase components are mixing, the water phase is prepared in a separate container and heated to 65° C. (150° F.).

The oil phase is then transferred to a lab agi-mixer which is capable of heating and cooling. The shear head speed is set to 4500 rpm. The oil phase is mixed therein for 30 seconds to insure a homogeneous mix. The water phase is added at a temperature of approx. 65° C. (150° F.) and the shear speed is then set to 5000 rpm. This resulting mixture is allowed to cool, with shearing, until the temperature of the mixture is approx. 48° C. (120° F.).

When the mixture reaches a temperature of 48° C. (120° F.), the improved fatty substance is added and the shearing is continued at 5000 rpm until the entire mixture reaches a temperature of approx. 15°-18° C. (60°-65° F.). The mixture is then allowed to mix at 5000 rpm for 10 minutes. The resulting margarine is finally transferred to plastic tubs and stored at 4° C. 40° F.)

EXAMPLE V

Cream Analog Containing the Improved Fatty Composition

| Components | Weight Percent |
|---|---|
| Heavy Cream (50% milkfat) | 50.00 |
| Skim Milk | 29.64 |
| Improved Fatty Substance (Example III) | 20.00 |
| Lecithin | 0.20 |
| Tween ® 60 (manufactured by ICI Americas, Inc., Wilmington, DE) | 0.16 |

The lecithin, Tween ® 60 and the improved fatty substance, as synthesized in Example III, are heated, while mixing, to approx. 48° C. (120° F.). The heavy cream and milk are mixed and heated to approx. 48° C. (120° F.) and added to the mixture consisting of the lecithin, Tween ® 60, and the fatty substance. The resulting mixture is homogenized at 500/2000 psi and finally cooled.

EXAMPLE VI

Ice Cream Analog Containing a Cream Analog Which Contains the Improved Fatty Composition

| Component | Weight Percent |
|---|---|
| Cream Analog (Example V) | 36.50 |
| 3.4% Milk | 25.00 |
| 67% Cane Sugar (liquid) | 17.60 |
| 30% Condensed Skim Milk | 7.50 |
| Water | 6.185 |
| Sweetened Whole Condensed Milk | 5.00 |
| Sugared Egg Yolks (24% fat) | 1.00 |
| Sugar | 1.00 |
| Gelatin (250 bloom) | 0.20 |
| Carrageenan | 0.015 |

First, ½ of the dry sugar is mixed with the carrageenan. Next ½ of the dry sugar is mixed with the gelatin and then dissolved in 500 milliliters of water at 48° C. (120° F.). The carrageenan/sugar mixture is then added to the liquid sugar and mixed well in a Hobart blender. The egg yolks, whole milk, condensed milk, and cream analog, as prepared in Example V, are mixed together. All mixtures are then combined together and the total mix is heated in a Groen kettle at approx. 48° C. (120° F.) for two hours. The mixture is next homogenized at 500/2000 psi, maintaining a mixture temperature of approx. 48° C. (120° F.). The resulting mixture is cooled overnight. Finally, vanilla extract and annato extract is added to taste and then the mixture is frozen.

What is claimed is:

1. A fatty composition comprising a mixture of a liquid nondigestible fatty material which has a melting point of 37° C. (98.6° F.) or below and a solid fatty material which has a complete melting point above 37° C. (98.6° F.), wherein said solid material has a particle size of 10 microns or less, wherein the weight ratio of liquid fatty material to solid fatty material is from about 1.5:1 to about 4:1 and wherein said solid fatty material is selected from the group consisting of solid nondigestible fatty materials and solid digestible sources of $C_{16}$ to $C_{26}$ saturated or transunsaturated fatty acids.

2. A composition according to claim 1 wherein the liquid fatty material is a polyol fatty acid polyester.

3. A composition according to claim 2 wherein the liquid polyol fatty acid polyester is selected from the group consisting of sugar fatty acid polyesters, sugar alcohol fatty acid polyesters, polyglycerol fatty acid polyesters, and mixtures thereof.

4. A composition according to claim 3 wherein the liquid polyol fatty acid polyester has at least 4 fatty acid polyester groups, and wherein the polyol is selected from the group consisting of sugars and sugar alcohols containing from 4 to 8 hydroxyl groups and wherein the fatty acids are selected from the group consisting of saturated and unsaturated fatty acids having from about 2 to about 24 carbon atoms, their geometric and positional isomers, and mixtures thereof.

5. A composition according to claim 4 wherein the solid fatty material is non-digestible.

6. A composition according to claim 5 wherein the solid fatty material is a polyol fatty acid polyester.

7. A composition according to claim 6 wherein the solid polyol fatty acid polyester is selected from the group consisting of sugar fatty acid polyesters, sugar alcohol fatty acid polyesters, polyglycerol fatty acid polyesters, and mixtures thereof.

8. A composition according to claim 7 wherein the solid polyol fatty acid polyester is a sucrose polyester, wherein the fatty acid ester groups consist essentially of short chain fatty acid radicals containing from about 2 to about 10 carbon atoms and long chain fatty acid radicals containing from about 20 to about 24 carbon atoms, the molar ratio of short chain to long chain radicals being from about 4:4 to about 3:5 and the degree of esterification being from about 7 to about 8.

9. A composition according to claim 7 wherein the solid polyol fatty acid polyester has at least 4 fatty acid polyester groups, and wherein the polyol of the polyester is selected from the group consisting of sugars and sugar alcohols containing from 4 to 8 hydroxyl groups and wherein the fatty acids are selected from the group consisting of saturated and unsaturated fatty acids having from about 2 to about 24 carbon atoms, their geometric and positional isomers, and mixtures thereof.

10. A composition according to claim 9 wherein each fatty acid group of the solid polyol fatty acid polyester has from about 8 to about 24 carbon atoms.

11. A composition according to any one of claims 5 to 10 wherein the polyol of the solid polyol fatty acid polyester is sucrose and wherein the liquid nondigestible fatty material is a fatty acid polyester of sucrose wherein each of the fatty acid ester groups of said liquid polyester contains from about 8 to about 24 carbon atoms.

12. A composition according to claim 7 wherein the solid polyol fatty acid polyester is a polyglycerol fatty acid polyester having from about 2 to about 30 esterified glycerol units and at least 75% of its hydroxyl groups esterified with fatty acids and wherein the fatty acids are selected from the group consisting of saturated and unsaturated fatty acids having from about 2 to about 24 carbon atoms, their geometric and positional isomers, and mixtures thereof.

13. A composition according to claim 12 wherein the solid polyglycerol fatty acid polyester has from about 5 to about 15 etherified glycerol units.

14. A composition according to claim 13 wherein the solid polyglycerol fatty acid polyester has from about 6 to about 10 etherified glycerol units.

15. A composition according to claim 14 wherein each fatty acid group of the solid polyglycerol fatty acid polyester has from about 8 to about 24 carbon atoms.

16. A composition of any one of claims 12 to 15 wherein the liquid nondigestible fatty material is a fatty acid polyester of sucrose wherein each of the fatty acid ester groups of said liquid polyester contains from about 8 to about 24 carbon atoms.

17. A composition of claim 4 wherein the solid fatty material is a digestible source of $C_{16}$ to $C_{26}$ saturated or trans unsaturated fatty acids.

* * * * *